United States Patent [19]  [11] 4,181,715
Kondo et al.  [45] Jan. 1, 1980

[54] NOVEL ANTIBIOTIC SUBSTANCE SF-1540 AND ITS DERIVATIVE, AND PROCESS FOR THE PRODUCTION THEREOF

[75] Inventors: Yasumitsu Kondo; Takashi Shomura; Hiroshi Watanabe; Tetsuro Watanabe; Shigeharu Inouye; Taro Niida, all of Yokohama, Japan

[73] Assignee: Meiji Seika Kaisha Ltd., Tokyo, Japan

[21] Appl. No.: 908,983

[22] Filed: May 24, 1978

Related U.S. Application Data

[63] Continuation-in-part of Ser. No. 751,437, Dec. 16, 1976, abandoned.

[30] Foreign Application Priority Data

Dec. 29, 1975 [JP] Japan .................................. 50/157469
Apr. 19, 1976 [JP] Japan .................................. 51/43659

[51] Int. Cl.² ............................................. A61K 35/00
[52] U.S. Cl. ................................... 424/122; 435/128; 435/898
[58] Field of Search .............. 424/122, 123; 195/80 R

[56] References Cited

U.S. PATENT DOCUMENTS 3,993,749 11/1976 Sehgal et al. ......................... 424/122

*Primary Examiner*—Jerome D. Goldberg
*Attorney, Agent, or Firm*—Flynn & Frishauf

[57] ABSTRACT

A novel antibiotic substance SF-1540 and a process for preparing the same which comprises culturing a substance SF-1540-producing microorganism belonging to the genus Streptomyces in a medium and isolating and recovering the substance SF-1540 from a cultured broth; a novel derivative of the substance SF-1540 and a process for preparing the same which comprises treating said antibiotic substance SF-1540 with methanol to form the corresponding antibiotic substance SF-1540 derivative.

7 Claims, 6 Drawing Figures

NOVEL ANTIBIOTIC SUBSTANCE SF-1540 AND ITS DERIVATIVE, AND PROCESS FOR THE PRODUCTION THEREOF

RELATED APPLICATION

This application is a continuation-in-part of our application Ser. No. 751,437, filed Dec. 16, 1976, now abandoned.

The present invention relates to a novel antibiotic substance and its derivative, and a process for the preparation thereof. More specifically, this invention relates to a novel antibiotic substance named SF-1540 and its derivative and to a process for preparing the same in which a substance SF-1540-producing microorganism belonging to the genus Streptomyces is cultured in a medium under aerobic condition and an active substance, substance SF-1540, which is produced in a cultured broth and exerts a potent inhibitory activity against moulds is recovered from said cultured broth. As a result of our further studies on the nature of the active substance isolated in a pure state, it has been confirmed that the active substance is a novel antibiotic different from known substances and named substance SF-1540.

As one example of the substance SF-1540-producing microorganisms belonging to the genus Streptomyces, there may be mentioned the strain named by us as *Streptomyces hygroscopicus* SF-1540, the morphological characteristics of which are as summarized below. This strain has been deposited under an accession No.2607 with Technical Research Institute of Microbial Industry, Agency of Industrial Science & Technology, Japan. (ATCC No. 31257)

I. Morphological Characteristics

Abundant aerial mycelium on starch agar medium, oatmeal agar medium, yeast-malt agar medium and tyrosine agar medium. Good sporulation. Straight branches without cluster-like branches. Aerial hyphae are terminated with compact closed spirals or short open spirals. Sclerotia not formed. Spore surface is warty under an electron-microscope. Spores are elliptical to short cylindrical in shape and $0.8$–$1.1 \times 1.1$–$1.4$ $\mu$ in size. Spore chains are in 10 or more spores per spore chain.

II. Characteristic Growth in Various Media

| Medium | Growth | Aerial mycelium | Soluble pigment |
|---|---|---|---|
| Sucrose-nitrate agar | Colorless | Scant, grey | None |
| Glucose-asparagine agar | Pale yellow | Scant, grey | None |
| Glycerol-asparagine agar | Pale yellow | Scant, white to grey | None |
| Starch agar | Good greyish yellow | Abundant, grey to greyish brown, gradually becoming hygroscopic | None |
| Oatmeal agar | Good, greyish yellow | Grey to greyish brown, gradually becoming hygroscopic | None to faint yellow |
| Yeast-malt agar | Good, pale yellowish brown | Scant, grey | None |
| Tyrosine agar | Good, brown | Abundant, grey, gradually becoming hygroscopic | None |
| Nutrient agar | Pale yellow | Very scant, white | None |

[Note] All culture temperatures of 28° C.

III. Physiological Characteristics (1) Temperature range for growth: Good growth at a temperature range of 15°–49° C. on starch-yeast agar medium.
(2) Gelatin liquefaction: Positive at 20° C. for 30 days.
(3) Hydrolysis of starch: Positive
(4) Coagulation of skim milk: Negative (at 28° C. and 37° C.) Peptonization of skim milk: Positive (at 28° C. and 37° C.)
(5) Melanin formation: Negative

IV. Carbon source utilization pattern (Pridham-Gottlieb's agar medium)

(1) Positive: D-glucose, D-fructose, D-mannitol, I-inositol, L-arabinose, rhamnose
(2) Doubtful: D-xylose, raffinose
(3) Negative: Sucrose Summing up morphological characteristics of the strain SF-1540 from the foregoing, aerial hyphae forms spirals and spore surface is warty. Color of growth is pale yellow to yellowish brown to greyish yellow. Aerial hyphae is greyish brown and gradually becomes hygroscopic.

These characteristics of the strain SF-1540 are in fair agreement with those of *Streptomyces hygroscopicus* which belongs to the genus Streptomyces. More specifically, the strain SF-1540 has been observed to have the following three points which are considered as characteristics of *Streptomyces hygroscopicus*. (1) Spiral is formed, (2) Greyish brown aerial hyphae grows and (3) Aerial hyphae becomes hygroscopic.

In comparison between the strain SF-1540 and *Streptomyces hygroscopicus* which has been described by Waksman in The Actinomycetes, Vol. 2, 230–231 (1961), their characteristics are generally common with each other, though some differences are observed, including formation of soluble pigment on sucrose-nitrate agar and glucose-asparagine agar and so on.

From the above, the strain SF-1540 has been reasonably regarded to belong to the species of *Streptomyces hygroscopicus* in view of the characteristics as specified in the above three points, though some differences are to be observed from the disclosure made by Waksman and we have, accordingly, named the strain SF-1540 *Streptomyces hygroscopicus* SF-1540 as distinguished from other publicly-known strains.

The strain SF-1540, as seen in other strains of the genus Streptomyces, is apt to be varied in its characteristics and may be easily variable artificially, for example, by means of ultraviolet ray, X ray, high-frequency wave, radiant ray or chemicals. Consequently, the strains usable in this invention include all of the variants which are capable of producing the substance SF-1540.

In the present process, the above strain is cultured in a culture medium containing those nutrients ordinarily utilizable by other microorganisms. As nutrient sources, there may be employed the well-known materials usually utilized for culture of organisms belonging to the genus Streptomyces. For instance, as a carbon source may be employed glucose, starch, glycerol, dextrin, sucrose, starch syrup, molasses, soy-bean oil and so on. Also, as a nitrogen source may be employed soy-bean meal, corn steep liquor, wheat embryo, cotton seed meal, ammonium sulfate, sodium nitrate and so on. In addition, inorganic salts such as calcium carbonate, sodium chloride, potassium chloride, a phosphate, etc., as well as organic and inorganic materials which may act to promote the growth of this strain and increase the production of the substance SF-1540 may be incorporated, if necessary.

In carrying the cultivation into practice, liquid culture may be made in the same manner as generally used for the production of antibiotics and, in particular, submerged culture is most preferable. Cultivation may be usually effected under aerobic condition and culture temperatures of 25°–35° C. are usually applied, but, in most cases, 28° C. may be applied. Maximum production of the substance SF-1540 is obtained in 2–5 days by both shaking and tank cultures.

The above-mentioned culture conditions may be selected and applied for the optimum ones depending upon the properties of the respective producing strains employed. The substance SF-1540 is included in both mycelia and cultured broth and may be extracted from both of them, separately. Alternatively, the cultured broth was made weakly acidic without any filtration, whereupon the substance SF-1540 is adsorbed onto mycelia or precipitated in situ and then only mycelia portions may be extracted. In carrying the extraction into practice, any well-known procedures usually employed for the recovery of fat-soluble natural products from a cultured broth are adaptable, since the substance SF-1540 is fat-soluble as apparent from the physicochemical properties thereof mentioned below.

As an example, the cultured broth of *Streptomyces hygroscopicus* strain SF-1540 and the aqueous solution obtained by removal of methanol from an aqueous methanol extract of mycelia is extracted with a water-immiscible organic solvent, e.g. ethyl acetate, whereby the substance SF-1540 is transferred into the organic solvent layer. The extract is concentrated under reduced pressure to leave a syrupy substance, from which a crude substance SF-1540 is precipitated by the addition of cyclohexane. The crude precipitate containing the substance SF-1540 is purified through a column chromatography, e.g. silica gel column chromatography using benzene-acetone (20:1) as a developing agent or Sephadex LH-20 (Pharmacia Co., Ltd.) using an organic solvent such as methanol, ethyl acetate and so on as a developing agent.

Physicochemical properties of the substance SF-1540, a pale yellow powder, produced according to the process of this invention are as shown below.

(1) Elemental analysis —Carbon, 65.16%; Hydrogen, 8.24%; Nitrogen, 2.17%; Oxygen, 23.79%.

(2) Molecular weight (measured by a vapor pressure method) —about 600.

(3) Melting point—131°–133° C.

(4) Optical rotation—$[\alpha]_D^{25}+31.6°$ (C=1, methanol)

Figure 1:
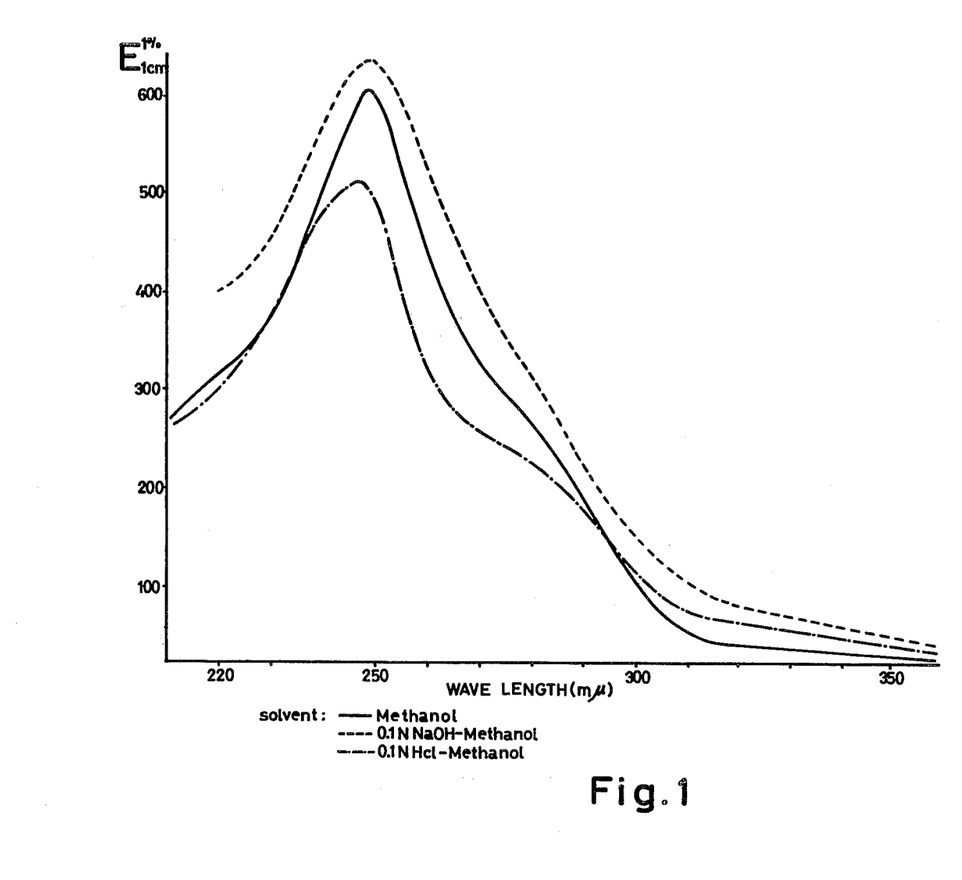

(5) Ultraviolet absorption spectrum—The ultraviolet absorption spectrum in a methanolic solution is as shown in FIG. 1. Maximum absorption—249 nm ($E_{1cm}^{1\%}$ 605); Shoulder—280 nm ($E_{1cm}^{1\%}$ 270).

Figure 2:
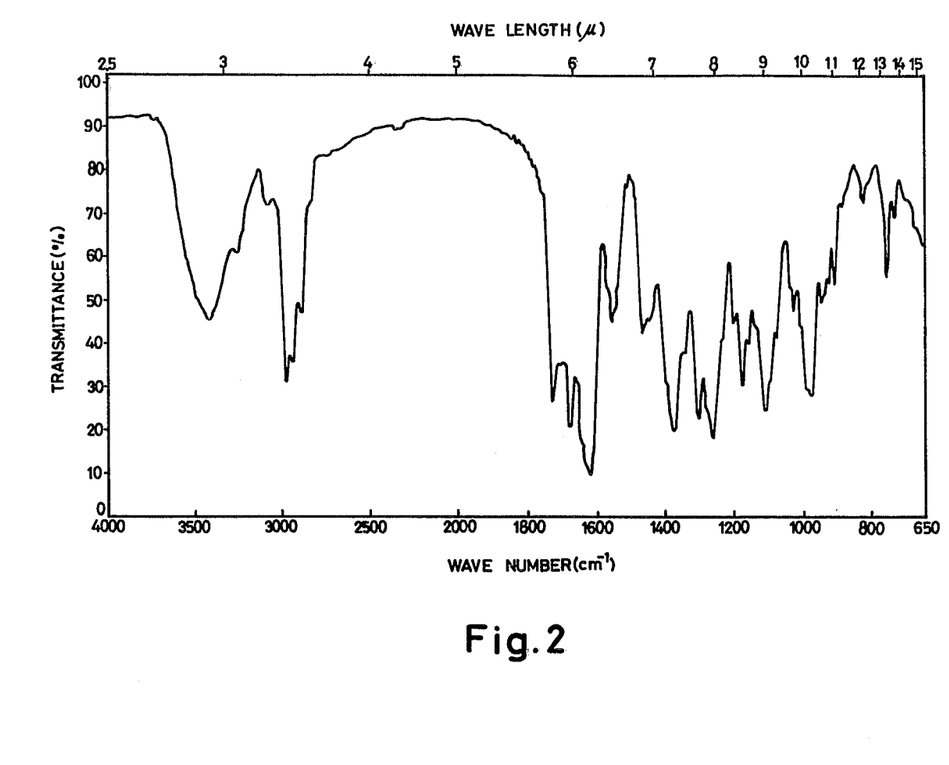

(6) Infrared absorption spectrum—The infrared absorption spectrum in a KBr tablet method is as shown in FIG. 2.

Figure 3:
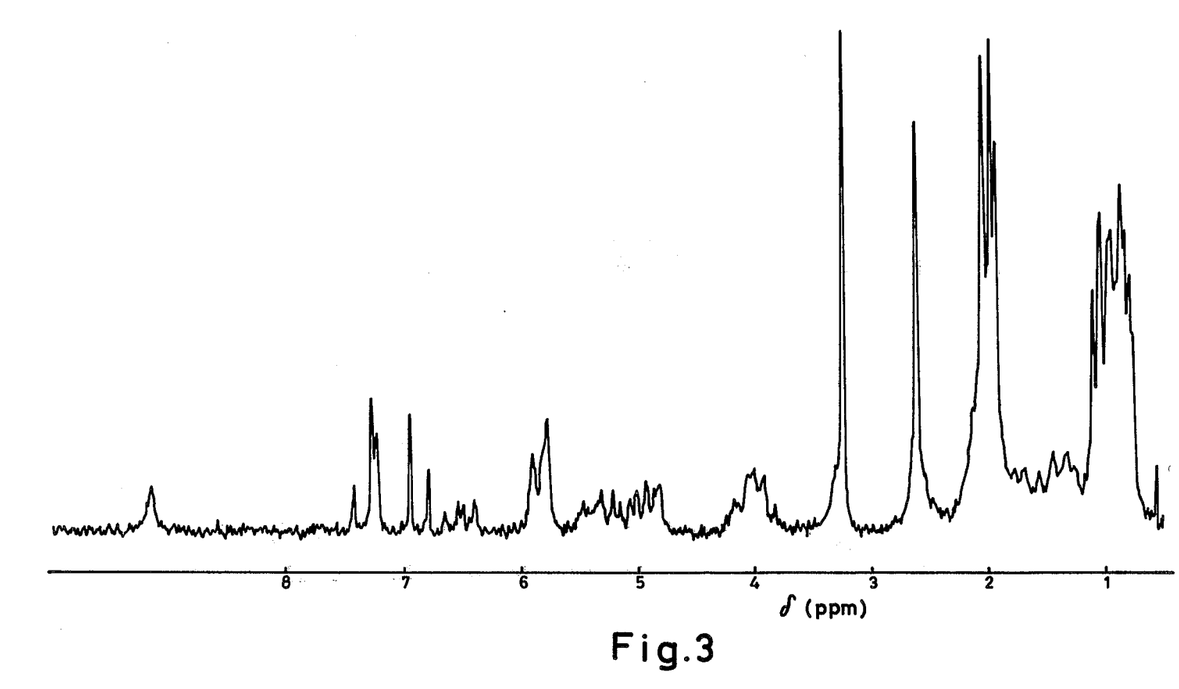

(7) Nuclear Magnetic Resonance spectrum—The NMR spectrum in CDCl$_3$, 100 MHz, is as shown in FIG. 3.

(8) Solubility in solvents—Soluble in methanol, ethanol, n-butanol, ethyl acetate, benzene, acetone, chloroform, carbon tetrachloride and ethyl ether. Insoluble in water and cyclohexane (9) Stability—Antibacterial activity decreased by approximately 70% in 0.02 N HCl and 0.02 N HaOH. Somewhat unstable to an acid and an alkali.

(10) Rf values in various chromatographies—Single spot having Rf value of 0.57 on a silica gel thin-layer chromatography (available from Merck & Co., Inc.) developed with chloroform-methanol (5:1), Rf value of 0.23 on the chromatography developed with benzene-acetone (2:1), Rf value of 0.31 developed with ethyl acetate (11) Color reaction—Positive to KMnO$_4$ and H$_2$SO$_4$; negative to ninhydrin.

The present invention further relates to a useful and new derivative of the above-mentioned antibiotic substance SF-1540 and to a process for preparing the derivative, As described above in detail, the antibiotic substance SF-1540 can be solvent-extracted and isolated from a cultured broth, for example of *Streptomyces hygroscopicus* SF-1540 and is an antimicrobial agent effective mainly against grampositive bacteria and various moulds.

The substance SF-1540 itself is, however, of a relatively high toxicity and, in case where its aqueous suspension is intraperitoneally given to mice, all animals died at a dose of not less than 5 mg./kg.

As a result of our further studies to prepare and test various derivatives thereof in order to improve such a disadvantage, it has been found that a new derivative can be formed by treating the substance SF-1540 with methanol and keep the antibiotic activity of the parent compound unchanged as it is, simultaneously with an acute toxicity reduced to at least one twentieth or less than that of the parent compound.

More specifically, the substance SF-1540 in its pure state or a crude material containing said substance can be dissolved in methanol or a methanol-containing mixture and the resulting solution is allowed to stand at a temperature of 5°–60° C., preferably room temperature, for several hours to several days to afford the derivative of substance SF-1540 (hereinafter referred to as "the present derivative"). At least one molar proportion of methanol is used with one molar proportion of substance SF-1540. For example, a solution of substance SF-1540 in methanol is left at room temperature for 2 days, whereby the substantially complete reaction proceeds to produce the present derivative quantitatively. In addition, it is feasible to employ as a starting material the crude substance SF-1540 which is with different purities and obtainable during the isolation stage from a cultured broth. However, the lower the purity of the starting material is, the slower the reaction proceeds, and where the crude substance SF-1540 with a purity of 80% is employed, the reaction may proceed by approximately 80% even through treatment with methanol at room temperature for one day, but not further, and some 20% of the starting material remains unreacted.

The present derivative obtainable from treatment of substance SF-1540 with methanol may be further purified, if required, according to the purification procedures for substance SF-1540. In order that the present derivative may be separated from unreacted substance SF-1540, it is particularly convenient to employ a column of Sephadex LH-20 and then develop said column with methanol.

Physicochemical properties of the derivative of this invention are as shown below.

The present derivative is a pale yellow powder and melts at 114°–116° C. in its amorphous form. The compound is relatively stable under neutral condition, but unstable under acidic and alkaline conditions.

Optical rotation: $[\alpha]_D^{20} + 21°$ (C=1%, CHCl$_3$).

Elementary analysis: C, 66.69; H, 8.62; N, 1.68; O, 23.96 (%).

Molecular weight: about 700 (measured by a vapor pressure method).

Figure 4:
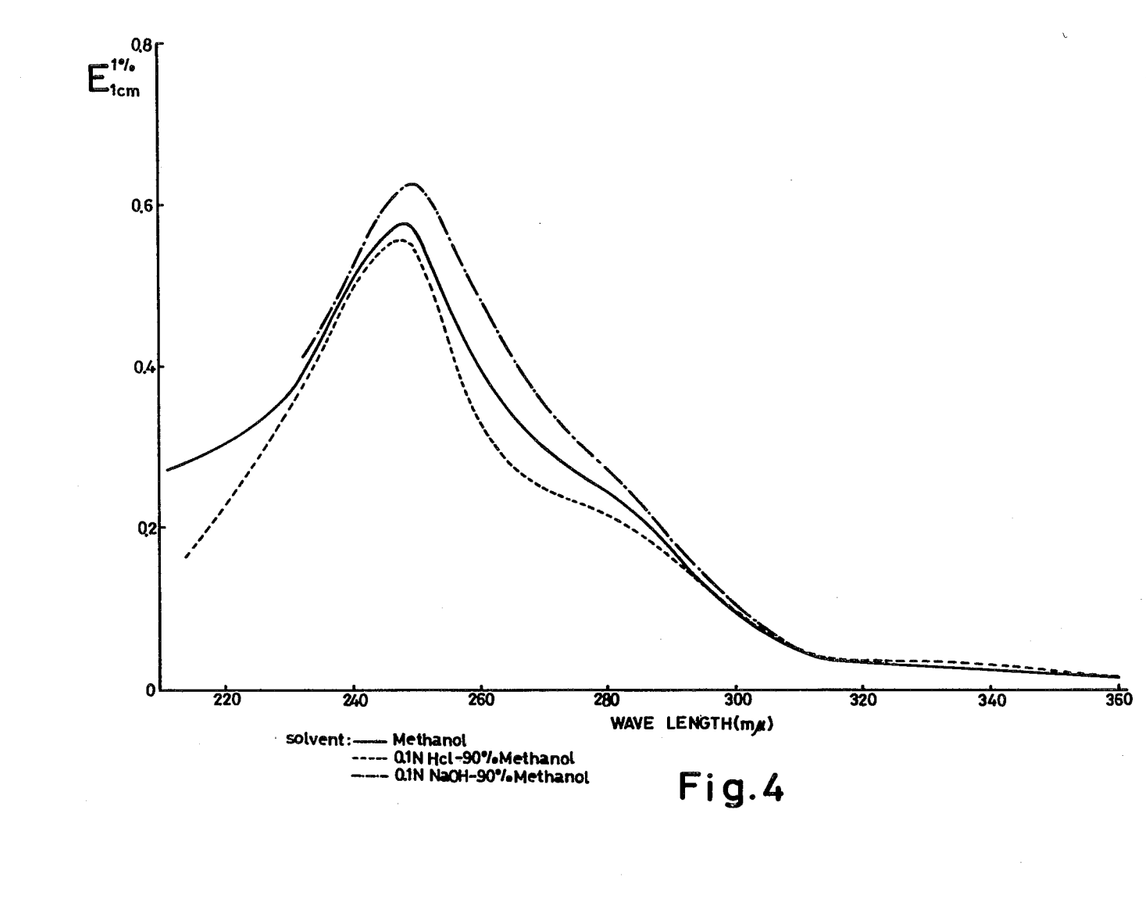

Ultraviolet absorption spectrum: The ultraviolet absorption spectrum in a methanolic solution (10 mcg./ml) is as shown in FIG. 4. Maximum absorption in neutral methanol 249 nm ($E_{1\ cm}^{1\%}$ 585).

Figure 5:
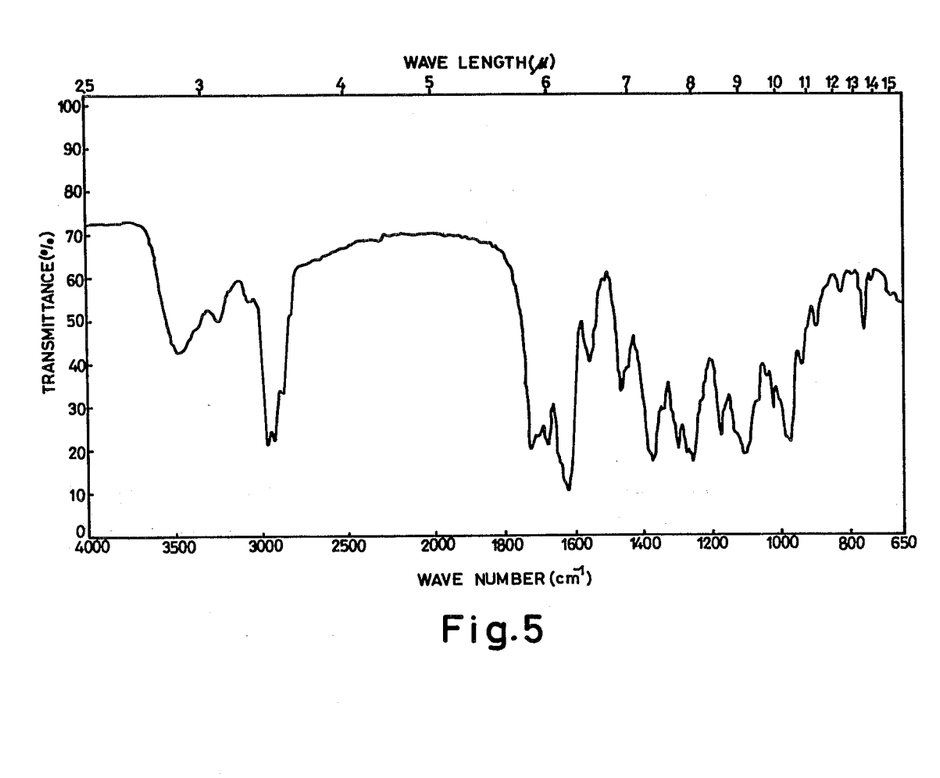

Infrared absorption spectrum: The infrared absorption spectrum in a KBr tablet method is as shown in FIG. 5.

Figure 6:
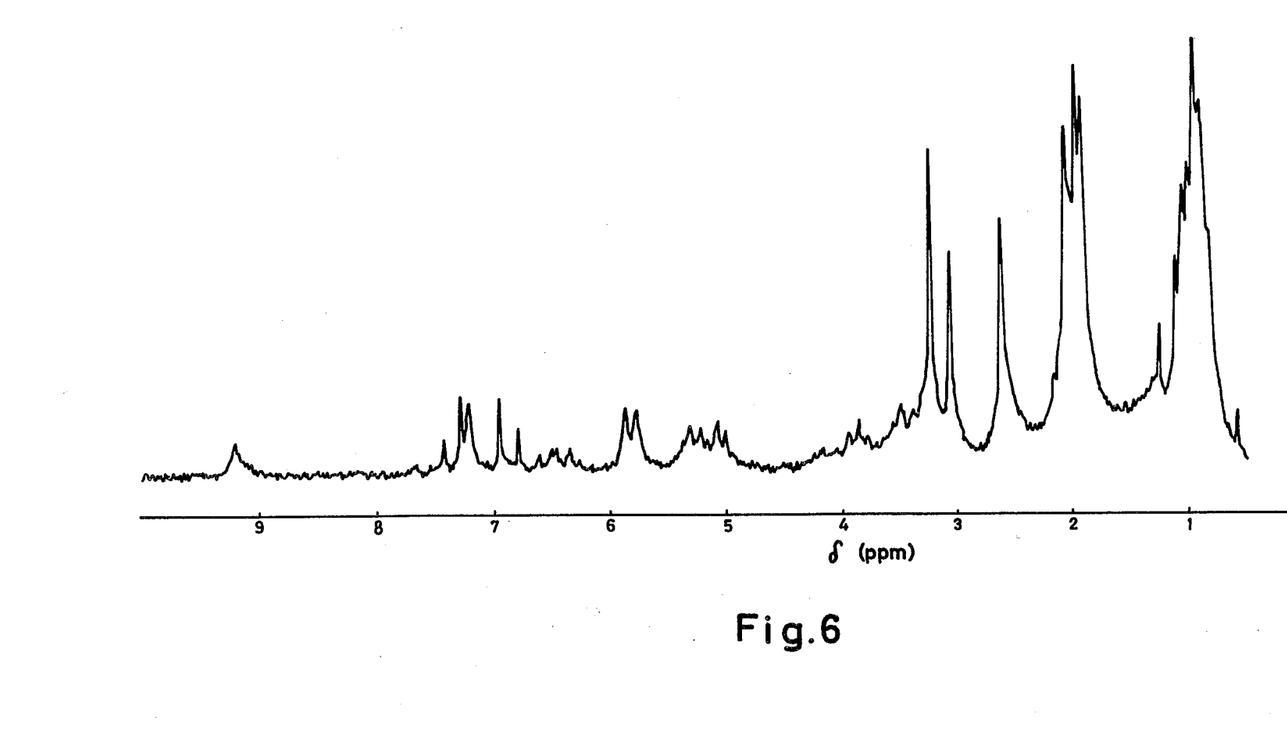

Nuclear Magnetic Resonance spectrum: The NMR spectrum in CDCl$_3$, 100 MHz, is as shown in FIG. 6.

Solubility in solvents: Soluble in methanol, ethanol, butanol, ethyl acetate, benzene, acetone, chloroform, carbon tetrachloride and ethyl ether and sparingly soluble in water.

Color reaction: Positive to potassium permanganate and sulfuric acid and negative to ninhydrin.

As particularly analogous compounds to the present derivative may be mentioned the substance SF-1540 as well as the substance SF-1540B which is disclosed and claimed in our co-pending Japanese Patent Application No. 34400/1976 filed on Mar. 31, 1976, both of which show a substantially identical ultraviolet absorption spectrum. However, the present derivative can be definitely distinguished from the above two compounds, based upon silica gel thin-layer chromatographies shown in the following Table 1.

Table 1

| | Rf value | | |
|---|---|---|---|
| | The present derivative | SF-1540 | SF-1540B |
| Benzene-acetone (2:1) | 0.35 | 0.23 | 0.05 |
| Ethyl acetate | 0.42 | 0.31 | 0.08 |
| Chloroform-methanol (5:1) | 0.67 | 0.57 | 0.17 |

In assay of the substance SF-1540 and the present derivative, there is used the following procedures. Potato.glucose.agar medium is used as a test medium. Test organism is *Piricularia oryzae*. By the assay using the above-mentioned materials, there is observed a linear relationship between logarithms of a concentration and inhibition zone in the substance SF-1540 and of the present derivative at 32 mcg/ml - 2 mcg/ml, showing correspondingly inhibition zones of 52.6–31.2 mm (Paper disc plate method). In the present derivative, the linear relationship is observed at a concentration of 32 mcg/ml - 2 mcg/ml showing correspondingly inhibition zones of 47.7–28.5 mm Antibacterial spectra of the substance SF-1540 and the present derivative against various microorganisms are shown in the following Table 2.

Table 2

| | MIC (mcg/ml) | | |
|---|---|---|---|
| Test organism | Substance SF-1540 | The present derivative | Medium |
| *Bacillus sublitis* ATCC 6633 | 6.25 | 12.5 | 1 |
| *Staphylococcus aureus* 209p | 12.5 | 12.5 | 1 |
| *Escherichia coli* | >100 | >100 | 1 |
| *Mycobacterium smegmatis* 607 | 25 | 25 | 2 |
| *Candida albicans* | 100 | >100 | 3 |
| *Saccharomyces cerevisiae* | 100 | 100 | 3 |
| *Saccharomyces chevalieri* | 0.78 | <0.39 | 3 |
| *Saccharomyces sake* | 50 | >100 | 3 |
| *Alternaria kikuchiana* | 3.125 | 12.5 | 4 |
| *Botrytis cinerae* | 3.125 | 6.25 | 4 |
| *Pellicularia sasakii* | 0.19 | 3.1 | 4 |
| *Muccor angulisporus* | >100 | >100 | 4 |
| *Leptosphaeri salvinii* | 0.39 | 0.1 | 4 |
| *Trichophyton asteroides* | 100 | 100 | 4 |
| *Piricularia orizae* | 0.78 | 0.1 | 4 |
| *Colletotrichum lagenarium* | 3.125 | 0.1 | 4 |
| *Fusarium oxysporum* | 100 | >100 | 4 |

[Note]
1: Bouillon media
2: Glycerin-bouillon media
3: Sabouraud's media
4: Potato-glucose-agar media As is apparent from the above results, the substance SF-1540 and the present derivative have characteristics in that they exert little antibacterial activity against gram-negative bacteria, but do not exert activity against gram-positive bacteria, yeast and mould. The activities of the present derivative are substantially identical to those of the parent compound, the substance SF-1540, but it exerts a far greater activity against certain moulds than the parent compound does.

In case where the present compound was intraperitoneally administered to mice, all animals survived at 15 mg./kg. and 50 mg./kg., whereas in case of the parent substance SF-1540, all animals died at 5 mg./kg. and survived at 2 mg./kg.

Inasmuch as other known antibiotic substances are not found which show the above-defined physicochemical and biological properties, the present substances are to be regarded as new antibiotic substances.

This invention will be more fully ilustrated by way of the following examples. However, it should be appreciated that various changes and modifications may be made within the scope of this invention, even if not specifically shown herein.

EXAMPLE 1

Spores of *Streptomyces hygroscopicus* strain SF-1540 (deposit number 2607) were inoculated to 1 l of a liquid medium containing 1% starch, 3% soybean meal (pH 7) (using ten Sakaguchi's flasks). Shaking culture was effected at 28° C. for 40 hours to obtain a seed culture. 35 l of a liquid medium containing 2.5% glucose, 2.0% wheat embryo, 0.5% soluble vegetable protein, 0.25% sodium chloride (pH 7.0) were inoculated with the seed culture. Cultivation was continued at 28° C. for 76 hours under aerated agitation (using two 50 l-jar fermentors).

Cultured broth was then adjusted to pH 3–4 with 6 N hydrochloric acid, whereupon the substance SF-1540 was transferred into mycelium fractions. To the broth was added a filter aid, Hyflo Super Cel, and mycelia were collected by filtration and then extracted with 9 l of methanol. The mycelia were filtered off to yield 11 l of an aqueous methanol solution.

The aqueous methanol solution thus obtained was concentrated under reduced pressure to 2.5 l of an aqueous solution. The solution was extracted three times with ethyl acetate (2.5 l), whereby the substance SF-1540 was transferred into the ethyl acetate phase, which was then dehydrated with anhydrous sodium sulfate and concentrated under reduced pressure to leave 30 g of an yellowish brown powder.

The yellowish brown powder containing the substance SF-1540 was extracted with cyclohexane to give 9.3 g of a brown powder containing the crude substance SF-1540 in cyclohexane-insoluble portions. The brown powder thus obtained was dissolved in a small amount of acetone and the resulting solution was chromatographed over a silica gel (800 ml) column packed with benzene using benzene-acetone (20:1) as a developing agent. Those fractions of Nos. 387–470 were collected which showed an activity against *Piricularia oryzae,* each fraction being 15 g. The collected fractions were concentrated under reduced pressure to yield 728 mg of the substance SF-1540 with a purity of 80% as a pale yellow powder. 350 mg of the so obtained pale yellow powder was dissolved in a small amount of acetone and the resulting solution was chromatographed over a silica gel (100 ml) column packed with benzene using benzene-acetone (20:1) as a developing agent. Those fractions of Nos. 421–443 were collected which showed an activity as seen above, each fraction being 10 g. The collected fractions were concentrated under reduced pressure to afford 65 mg of the substance SF-1540 as a pale yellow powder.

EXAMPLE 2

350 mg of the substance SF-1540 (728 mg) obtained as a pale yellow powder with a purity of 80% in the above Example 1 was dissolved in a small amount of ethyl acetate and the resulting solution was chromatographed over a Sephadex LH-20 (300 ml) column packed with ethyl acetate using ethyl acetate as a developing agent. By each 5 g fractionation, fractions No. 17–20 were subjected to a silica gel thin-layer chromatography (benzene:acetone=2:1), whereby a single spot of the substance SF-1540 was detected. These fractions were concentrated under reduced pressure to afford 168 mg of a pale yellow powder.

EXAMPLE 3

500 mg of the crude substance SF-1540 (with a purity of 80%) obtained in the above Reference example was dissolved in 10 ml of methanol and the resulting solution was left at room temperature for 24 hours. The mixture was concentrated and passed through a Sephadex LH-20 (300 ml) column which was then developed with methanol. Effluents were in each 10 g portion collected and those fractions of Nos. 20–30 were recovered and concentrated to dryness to afford 184 mg of the present derivative. M.P. 114°–116° C.

Separately, 30 mg of unreacted substance SF-1540 was recovered from those fractions of Nos. 17–18.

EXAMPLE 4

500 mg of the substance SF-1540 with a purity of not less than 99% was dissolved in 10 ml of methanol and the resulting solution was left at room temperature for 2 days. The mixture was concentrated to dryness and, after addition of 20 ml of fresh methanol, again concentrated to dryness to leave 490 mg of a powder substantially composed of the present derivative solely.

ANTITRICHOMONAS ACTIVITY TESTS USING MICE

Test Compounds: SF-1540-A' (substance SF-1540 treated with methanol). Control—Flagyl (MNZ, available from Shionogi Seiyaku K.K., Japan)=Metronidazol—1'-(2'-Hydroxyethyl)-2'-methyl-5'-nitroimidazole

Test Procedures

1. Test protozoa strain: *Trichomonas vaginalis* Ito
2. Host animals: SLC-ICR strain male mice of average body weight of 20 g. and 5-week age, each group consisting of 5 animals.
3. Inoculation of protozoa: Protozoa were inoculated to Bacto-Kupferberg Trichomonas base (Difco; 20% calf serum added), cultivation was conducted at 37° C. for 24 hours, propagated protozoa were collected and centrifuged at 1500 r.p.m. for 5 minutes and then washed twice with centrifugation in sterilized Locke-Ringer's solution. The supernatant was discarded and the residue was diluted with sterilized Ringer's solution so as to have a protozoal number of $500 \times 10^4$ ml. Each 0.2 ml. portion (the protozoal number of $100 \times 10^4$) was inoculated to mice at subcutaneous sites of the back thereof wherein fur was previously removed.
4. Preparation of test samples: Each test compound was aseptically weighed, finely-divided in a sterilized mortar and then suspended in a 1% CMC solution to form suspensions of given concentrations.
5. Dose and administration: The SF-1540-A' was used at 3 dose levels: 50 mg./kg. (1 mg./0.2 ml./mouse/day), 25 mg./kg. (0.5 mg./0.2 ml./mouse/day) and 12.5 mg./kg. (0.25 mg./0.2 ml./mouse/day), while Flagyl as control was used at 2 dose levels: 25 mg./kg. (0.5 mg./0.2 ml./mouse/day) and 12.5 mg./kg. (0.25 mg./0.2 ml./mouse/day). After 24 hours from protozoa inoculation, the SF-1540-A' was given subcutaneously and Flagyl orally once a day for 6 days (Total, 6 times). As control, each 0.2 ml. portion of a 1% CMC solution was subcutaneously administered.

Test Results

Formation of an abscess at a subcutaneous site of the back of a host animal was visually detectable for its protuberance after 48 hours from the protozoa inoculation.

In Control Group with 1% CMC, formation of raised abscess was observed after 2 days from the protozoa inoculation, further bulge was seen after 4 days and maintained at approximately equal size until the 7th day when animals were sacrificed.

In Group with the SF-1540-A' at 50 mg./kg. and 25 mg./kg., reduction in bulged abscess was observed after 3 administrations, and thereafter a somewhat reduced tendency was seen. In Group with the SF-1540-A' at 12.5 mg./kg., a somewhat lesser size of bulge was constantly observed until animals were sacrificed, as compared with the above Control Group.

In Group with Flagyl at 25 mg./kg., a remarkable reduction in abscess was observed after 3 administrations, and only a slight bulge was seen upon sacrifice so that a prominent therapeutic effect can be supposed.

Size of abscess was measured when sacrificed and cultivated to confirm effectiveness of the test compound after 24 hours from the 6 administrations. In Groups with the SF-1540-A' and with Flagyl at 25 mg./kg., abscess disappeared and then an organized pattern into a connective tissue was observed.

When the above test results were tested according to Tukey method upon factorial analysis of repetitive one-way layouts, the difference in the ITO strain between Groups with the SF-1540-A' and Flagyl at 25 mg./kg. and Group with 1% CMC was observed as significant at the 1% level of significance. The difference between Group with Flagyl at 12.5 mg./kg. and Group with 1% CMC was significant at the 5% level of significance, while no significant difference was observed between Group with the SF-1540-A' at 12.5 mg./kg. and Group with 1% CMC. Further, no significant difference was observed between Group with the SF-1540-A' at 25 mg./kg. and Groups with Flagyl at 25 mg./kg. and 12.5 mg./kg.

From the above-recited experimental results, it can be expected that the SF-1540-A' at 50 mg./kg. exerts the same level of effects as Flagyl at 25 mg./kg. does, and it has been observed that the SF-1540-A' at 25 mg./kg. shows the same level of therapeutic effects as Flagyl at 12.5 mg./kg.

The substance SF-1540-A' of this invention is useful as an agricultural fungicide, especially as a preventive and curative against rice blast, which will be more fully illustrated by the following Experiments.

EXPERIMENT 1

Preventive and Curative Effects Against Rice Blast

Rice plant seedlings (variety: Jukkoku) were cultivated in unglazed pots on a turntable, each having a diameter of 9 cm., and sprayed at the 4-leaf stage with a test liquid preparation of the indicated concentration in an amount of 35 ml. per two pots by means of a spray gun under a pressure of 2 kg./cm.$^2$. After air-drying, the host plants were placed in a moisture room at 25° C. and inoculated by spraying with a suspension of spores of rice blast pathogenic fungus (*Pyricularia oryzae*).

The host plants were kept in the moisture room and then moved to an air conditioning room. After 5 days, the number of diseased spots developed over leaves were counted and a preventive and curative value was calculated therefrom according to the following equation:

Preventive and curative value (%) =

$$\frac{\text{(Number of diseased spots per leaf in non-treated groups)} - \text{(Number of diseased spots per leaf in treated groups)}}{\text{(Number of diseased spots per leaf in non-treated groups)}} \times 100$$

The results are summarized in the following Table.

Table 3

| Group | Concentration (ppm) | Average number of diseased spots per leaf | Preventive & curative value (%) | Phytotoxicity |
|---|---|---|---|---|
| Substance SF-1540-A' | 25 | 11.5 | 62 | — |
| " | 50 | 5.0 | 79 | — |
| " | 100 | 4.0 | 83 | — |
| Control (Blasticidin S) | 5 | 3.6 | 85 | — |
| Non-treated | — | 23.9 | 0 | — |

As illustratively shown in the Experiment, the substance SF-1540-A' of this invention exhibits a remarkable effect for preventing and curing rice blast over a wide concentration range without any phytotoxicity and thus can provide a useful agricultural fungicide.

In applying the substance SF-1540-A' of this invention as an agricultural fungicide, it may be either employed alone or in admixture with a suitable carrier to formulate it into a form of wettable powders, dusts, granules, fine granules, emulsions and the like and also applied in admixture with other agricultural fungicides, insecticides, nematocides, herbicides, plant growth regulators, fertilizers and the like. Its application is not limited to any specific combination for use.

In the case where the substance SF-1540-A' of this invention is to be used as liquid formulations, it is desirable to adopt a concentration range of 5–500 ppm in sprayable liquid formulations. In case of dusts, it is desirable to use the active substance in a range of 0.1–3%. Where applied to the surface of a dry or paddy field, it is desirable to apply the substance SF-1540-A' so as to provide a ratio of 3.0–500 g. per 10 acres.

Application of the substance SF-1540-A' as an agricultural fungicide will be more fully illustrated by way of the following examples wherein all parts are given by weight unless otherwise stated.

A. Wettable Powders

Five parts of the substance SF-1540-A', 57 parts of kaolin, 30 parts of diatomaceous earth, 5 parts of polyoxyethylene alkylaryl ether, and 3 parts of sodium lignosulfonate were uniformly admixed and, when used, suspended in water at a proper concentration and then applied as sprayable suspensions or suspensions for a paddy field.

B. Dusts 0.5 Part of the substance SF-1540-A' and 99.5 parts of talc were uniformly admixed and pulverized to form dusts, which are applicable as such.

C. Granules

To 3 parts of the substance SF-1540-A', 3.5 parts of sodium lignosulfonate and 93.5 parts of clay were added 22 parts of water. The resulting mixture was kneaded, granulated, shaped and dried to form granules which are spread as such over the surface of a paddy field.

When the substance SF-1540-A' is used as an antiprotozoal pharmaceutical for treating humans, it is administered orally in an amount of from 200 to 1000 mg. per adult per day. When applied in tablet form for vaginal use, it is administered in an amount of from 20 to 500 mg. per adult per day.

As the pharmaceutically acceptable carriers for the antiprotozoal compositions of this invention, there may be mentioned, for example, cellulose, hydroxypropyl cellulose, hydroxypropyl methyl cellulose, carboxymethyl cellulose, methyl cellulose, carboxymethyl cellulose calcium salt, cellulose acetate phthalate, hydroxypropyl cellulose phthalate, starch, hydroxypropyl starch, gum arabi, gelatin, sodium alginate, calcium lactate, mannitol, polyvinyl pyrrolidone, a dibasic acid such as phthalic acid, succinic acid and maleic acid, a half-ester of a dibasic acid such as phthalic acid, succinic acid and maleic acid, a monoester of a dibasic acid with polyvinyl alcohol, polyols such as polyvinyl alcohol, saccharoids and so on.

The active ingredient may be mixed with one or more carriers mentioned above according to an ordinary method to prepare the antiprotozoal compositions of this invention.

We claim:

1. An antibiotic substance SF-1540 which has the following physicochemical properties:

an optical rotation of $[\alpha]_D^{20} = +31.6°$ in methanol, an elementary analysis of 65.16% carbon, 8.24% hydrogen, 2.17% nitrogen and 23.79% oxygen, an ultraviolet absorption spectrum shown in FIG. 1, an infrared absorption sprectrum shown in FIG. 2 and a nuclear magnetic resonance spectrum shown in FIG. 3, a color reaction positive to potassium permanganate and sulfuric acid and negative to ninhydrin, sparingly soluble in water and cyclohexane, and soluble in methanol, ethanol, acetone, chloroform, ethyl acetate, n-butanol, benzene, carbon tetrachloride and ethyl acetate.

2. A process for production of the antibiotic substance SF-1540 as defined in claim 1 which comprises culturing Streptomyces hygroscopicus SF-1540 (ATCC 31257) in a culture medium under aerobic conditions until substantial antibiotic activity has been imparted to said medium and isolating and recovering the substance SF-1540 from the cultured broth.

3. A process according to claim 2 wherein said microorganism is cultured at a temperature of from 25° to 35° C. for from 2 to 5 days.

4. A process according to claim 2 wherein said culture medium contains glucose, wheat embryo, soluble vegetable protein and sodium chloride.

5. A derivative of the antibiotic substance SF-1540 as defined in claim 1 which has the following physicochemical properties:

an optical rotation of $[\alpha]_D^{20} = +21°$ in chloroform, an elementary analysis of 66.69% carbon, 8.62% hydrogen, 1.68% nitrogen and 23.96% oxygen, an ultraviolet absorption spectrum shown in FIG. 4, an infrared absorption spectrum shown in FIG. 5 and a nuclear magnetic resonance spectrum shown in FIG. 6, a color reaction positive to potassium permanganate and sulfuric acid and negative to ninhydrin, sparingly soluble in water, and soluble in methanol, ethanol, acetone, chloroform and ethyl acetate.

6. An antiprotozoal composition comprising an effective antiprotozoal amount of the derivative of SF-1540 as defined in claim 5 and a pharmaceutically acceptable carrier.

7. An agricultural composition comprising an effective fungicidal amount of the derivative of SF-1540 as defined in claim 5 and a carrier.

* * * * *